US005350372A

United States Patent [19]

Ikeda et al.

[11] Patent Number: 5,350,372

[45] Date of Patent: Sep. 27, 1994

[54] SOLVENT CONTAINER WITH A CONNECTER FOR COMMUNICATING WITH A DRUG VIAL

[75] Inventors: Koji Ikeda, Osaka; Hitoshi Futagawa, Kusatsu; Toshihiro Kikuchi, Suita; Minoru Honda, Otsu; Masanobu Iwasa, Osaka, all of Japan

[73] Assignee: Nissho Corporation, Osaka, Japan

[21] Appl. No.: 62,541

[22] Filed: May 18, 1993

[30] Foreign Application Priority Data

May 19, 1992 [JP] Japan .................................. 4-152925

[51] Int. Cl.[5] .............................................. A61B 19/00

[52] U.S. Cl. ..................................... 604/414; 141/329

[58] Field of Search ................................ 604/411-416; 141/312, 319, 320, 322, 329, 330; 206/219, 222

[56] References Cited

U.S. PATENT DOCUMENTS 4,583,971 4/1986 Bocquet et al. ........................ 604/82
4,614,267 9/1986 Larkin ................................ 206/221
4,757,911 7/1988 Larkin et al. ........................ 206/221
4,936,841 6/1990 Aoki et al. .......................... 604/413

OTHER PUBLICATIONS

English Translation of JP-A-H2-4375.

*Primary Examiner*—Jerome L. Kruter
*Attorney, Agent, or Firm*—Birch, Stewart, Kolasch & Birch

[57] ABSTRACT

A solvent container to be used in combination with a drug container or vial, which comprises a flexible container body containing a solvent therein and having a mouth covered with a self-sealing member, a guide capsule having an open end sealed by a sealing member and being removably mounted on the mouth of the container body; and a double-pointed hollow needle having a sharp piercing edge at each end and being slidably arranged in the guide capsule to constitute a means for communicating the container body with the drug vial in cooperation with the guide capsule.

6 Claims, 11 Drawing Sheets

SOLVENT CONTAINER WITH A CONNECTER FOR COMMUNICATING WITH A DRUG VIAL

BACKGROUND OF THE INVENTION

1. Field of the Invention

The present invention relates to a solvent container with a means for communicating with a drug vial. More particularly, it relates to a solvent container containing a solvent and having a means for communicating with a drug vial containing a dry drug adapted to be mixed with the solvent just before use to administrate it as a liquid medicine to a patient.

2. Description of the Background Art

In medical facilities such as hospitals, dry drugs contained in a drug container or vial have been used for intravenous drip by dissolving it in a suitable solvent such as distilled water, a physiological saline, a glucose solution or a solution of an other drug.

In order to simplify such operations, there have been proposed, for example, in JP-T- S61-501129, JP-A-H2-1277 and JP-U- S63-135642 (Japanese Utility Model), various drug delivery systems of the kind wherein a capsule including a drug vial therein is connected in series with a flexible container containing a dose of a solvent and adapted to allow the drug vial to aseptically communicate the flexible container just before use.

JP-T- S61-501129, which corresponds to U.S. Pat. No 4,583,971, discloses a closed drug delivery system comprising a flexible container having a liquid diluent therein, a capsule coupled to the flexible container, a drug vial having a drug therein adapted to be mixed with the diluent, said drug vial being supported in the capsule by a supporting means of the capsule, and a coupling means for coupling the capsule to the interior of the flexible container. In this system, the drug vial is communicated with the flexible container by a communicating means arranged in the coupling means, thus making it possible to aseptically mix the drug with the solvent.

JP-A- H2-1277, which corresponds to U.S. Pat. No. 4,936,841, discloses a fluid container comprising a flexible container containing a diluent, a capsule having a cylindrical connecting portion at its one end and being connected to a mouth of the flexible container at the connecting portion, a drug container held in the capsule, and a communicating member for communicating the flexible container with the drug container. In use, the communicating means is firstly pierced into the drug vial and then pierced into the flexible container to communicate the flexible container with the drug container. Since the flexible container is communicated with the drug container in the closed system, it is possible to aseptically mix the drug with the solvent.

JP-U- S63-135642 discloses a drug delivery system comprising a solvent container containing a diluent therein, a drug container or vial containing a dry drug and arranged in series with the flexible container, and a double pointed hollow needle slidably supported by a ring removably arranged in the drug container, the hollow needle being adapted to be pierced at one end into a rubber stopper of the drug container and at the other end into a rubber plug of the flexible container to aseptically connect two containers just before use.

All the above drug delivery systems of the prior art may be applied for various vials on the market. However, the drug delivery system of JP-T- S61-501129 requires a great number of different parts and makes it troublesome to open the passage between the vial and the diluent container as the opening of the passage is carried out by manually breaking a frangible member arranged between the vial and the diluent container. In addition, if the frangible member is broken defectively, a flow of the solvent is prevented because of a defective fracture of the frangible member, resulting in increase in a time for dissolving the drug in the solvent.

The drug delivery system of JP-A- H2-1277 has been improved in protection from contamination by foreign substances and in simplification of operations, as compared with that of JP-T- S61-501129. However, it also requires a great number of different parts and is complex in structure as the communicating member includes a controlling mechanism for controlling the order of fluid communication.

On the other hand, the drug delivery system of JP-U-S63-135642 is small in the number of parts and relatively easy to operate. However, it is required to apply a large external force to the system to communicate the vial with the liquid container. Further, it is required to remove the supporting ring and the double pointed needle from the solvent container after mixing the drug with the solvent to attach an infusion set to the plug of the solvent container. Thus, it is troublesome to handle. Also, there is a fear of leakage of the drug solution since the solvent container must be turned upside down after removal of the double-pointed needle to insert an needle of the infusion set to the plug of the solvent container.

SUMMARY OF THE INVENTION

It is therefore an object of the present invention to provide a solvent container which is easy to produce, easy to operate aseptically, free from leakage of a drug solution, and small in the number of parts.

The above and other objects of the present invention are achieved by providing a solvent container with a means for communicating with a drug vial, comprising:

- a flexible container body containing a solvent and having a mouth covered with a self-sealing means;
- a guide capsule having an open end at one end and being removably mounted on the mouth of said flexible container body at the other end, said open end being sealed by a sealing member; and,
- a double-pointed needle having a sharp piercing edge at each end and a hub at its central part, said needle being slidably arranged in said guide capsule to constitute a means for communicating with a drug body in cooperation with said guide capsule;
- an inner wall of said guide capsule having one or more vertical guide grooves for holding said double-pointed needle and for guiding said double-pointed needle towards the mouth of said flexible container, said guide capsule having a partition wall with a hole for insertion of the piercing edge of said double-pointed needle into said mouth of said container body through said self-sealing means.

The solvent container of the present invention is used in combination with a drug container or vial containing a dose of a dry drug such as, for example, powder drugs, freeze-dried drugs and solid preparations, and having a mouth sealed by a rubber stopper. Commercially available drug vials may be used for this purpose.

In use, the sealing member is peeled off from the open end of the guide capsule and then a drug vial is pushed in the guide capsule through the open end thereof. By pushing the drug vial in the guide capsule, the double-pointed needle is forced to move toward the mouth of the container body along the guide grooves of the guide capsule until the hub thereof comes into contact with the partition wall of the guide capsule. During movement of the double-pointed needle, the piercing ends of the needle pierce the rubber stopper of the container body and that of the drug vial, thereby communicating the container body with the drug vial through the double-pointed needle.

BRIEF DESCRIPTION OF THE DRAWINGS

The above and other objects, features advantages of the present invention will become apparent from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

Figure 1:
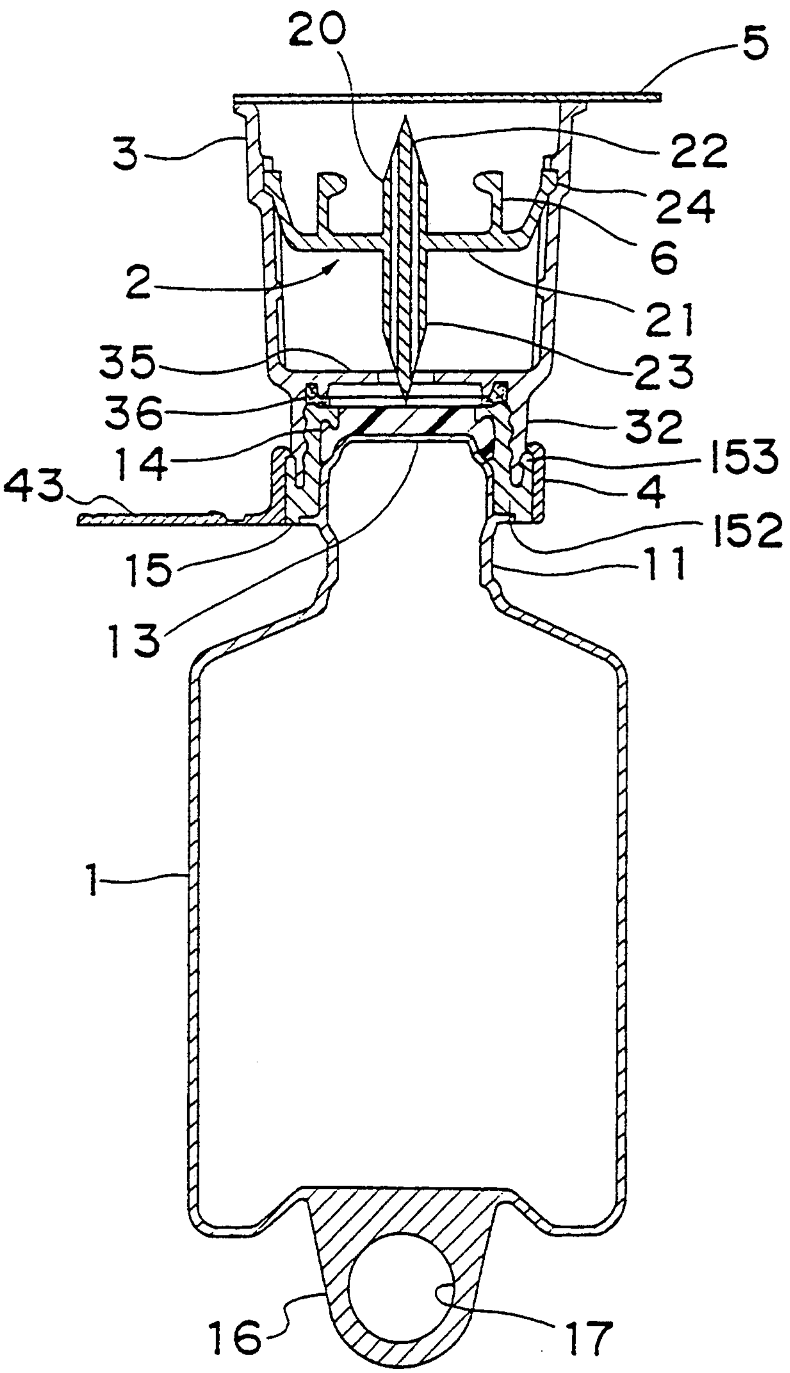
FIG. 1 is a schematic sectional view of a solvent container illustrating a preferred embodiment of the present invention.

Referring now to FIG. 1, there is shown a solvent container of the present invention, comprising a flexible container body 1 having a mouth 11, a double-pointed needle 2 and a guide capsule 3 removably mounted on the mouth 11 of the container body 1 and fixed thereto by means of a lock ring 4. The free end or an open end 38 of the guide capsule 3 is sealed by a sealing member 5. The double-pointed needle 2 is arranged in the guide capsule 3 so as to be moved downward when external force is applied thereto.

The flexible container body 1 is a deformable vessel, usually of a relatively soft resin such as polyethylene, polypropylene and polyesters, having a mouth 11 at one end and at the opposite end a closed bottom with a tab 16 serving as a hanging. The container body 1 contains a dose of a solvent such as distilled water, a physiological saline, a glucose solution or a solution of an other drug dissolved in a suitable solvent, but such a solvent has been omitted from the drawings for convenience sake.

Figure 2:
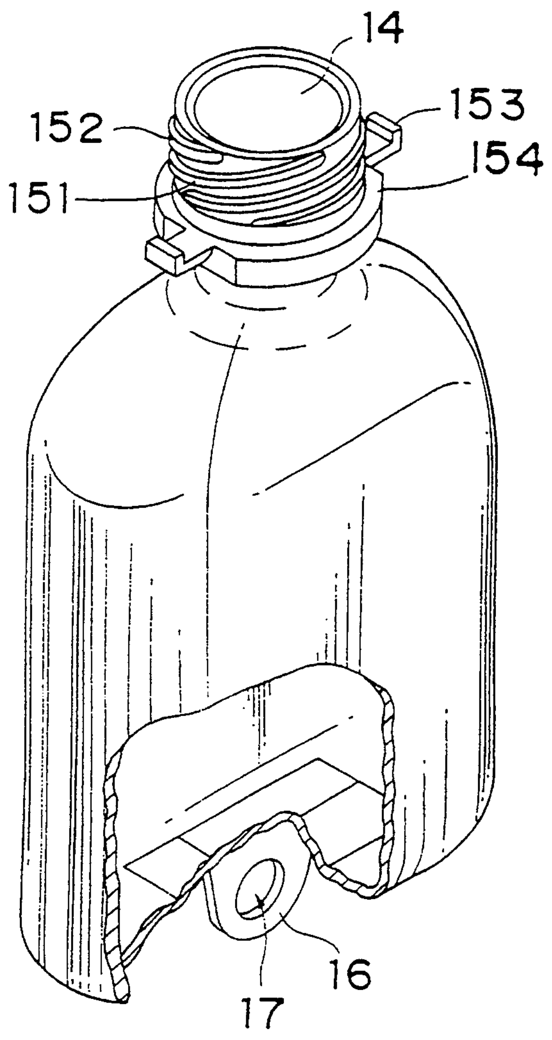
FIG. 2 is a partially cutaway perspective view of a flexible container body used in the solvent container of FIG. 1.

As shown in FIGS. 1 and 2, the mouth 11 of the container body 1 is sealed by an integrally molded sealing membrane 13 and covered with a self-sealing means. The self-sealing means is composed of a rubber stopper 14 and fixed to the mouth 11 by a covering member 15.

The rubber stopper 14 is a disk-like member, usually of butyl rubber, natural rubber or butadiene rubber, having a self-sealing property. The rubber stopper 14 is put on the sealing membrane 23 of the container body 1 and pressed against the mouth 11 of the container body 1 by the covering member 15, like as the conventional bottles. The attachment of the rubber stopper 14 may be carried out by fitting the rubber stopper 14 in the covering member 15, fitting the covering member 15 on the mouth of the container body 1, and then thermowelding a side wall 152 of the covering member 15 to the mouth 11 of the container body 1.

The covering member 15 is a cylindrical member provided in a side wall 152 thereof with a male screw 151 for engagement with the guide capsule 3. At the lower part of the covering member 15 adjacent to the male screw 151, there is an annular flange 154 integrally molded with the covering member 15 and having two L-shaped fastening lobes 153 extending outwardly therefrom in opposite directions.

These fastening lobes 153 are fitted in stepped portions 33 of the guide capsule 3 and fixed thereto by the lock ring 4 to prevent the guide capsule 3 from coming off. When separating the guide capsule 3 from the container body 1, the fastening lobes 153 are taken off from the stepped portions 33 after removing the lock ring 4 and then the guide capsule 3 is turned clockwise or counterclockwise to loosen the screw.

The tab 16 is provided with a hole 17 and integrally and foldably molded with the bottom of the container body 1, like as an integrated hinge. Thus, the tab 16 can be hung on a hook or hanger at its hole 17 to hold the solvent container in a suitable position after dissolution of the dry drug with the solvent.

Figure 3:
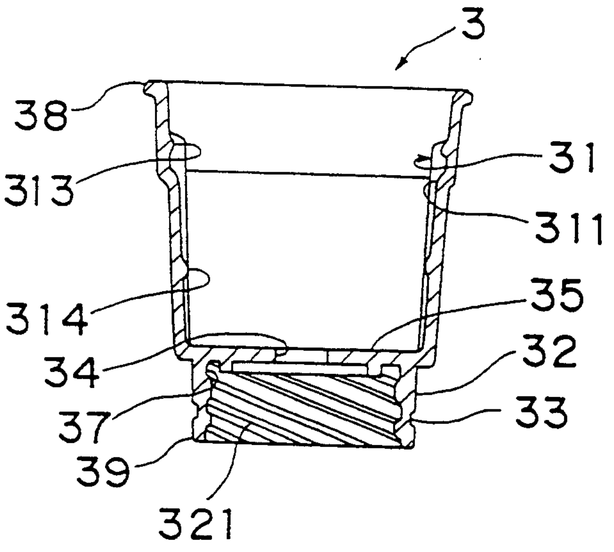
FIG. 3 is a sectional view of a guide capsule used in the solvent container of FIG. 1.
Figure 4:
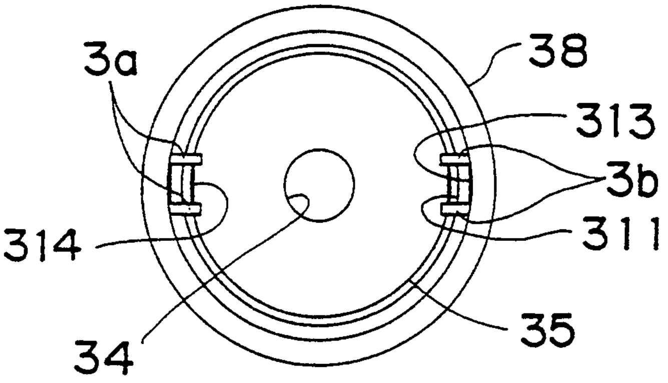
FIG. 4 is a top view of the guide capsule of FIG. 3.
Figure 5:
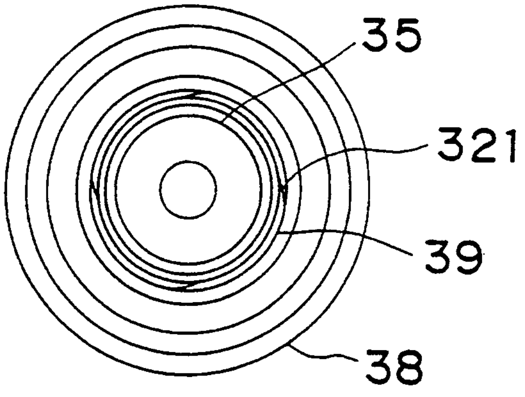
FIG. 5 is a bottom view of the guide capsule of FIG. 3.

As best shown in FIGS. 3 to 5, the guide capsule 3 is a cylindrical hollow member, usually of a synthetic resin such as polyethylene, polypropylene, polyester, polyvinyl chloride, polycarbonate, ABS resins and the like, having an open end 38 and a connecting end 39 reduced in diameter and partitioned by a partition wall 35 to form a connecting portion 32. The open end 38 is sealed by a sealing member 5 in the form of a sheet or a film, as shown in FIG. 1.

The guide capsule 3 is provided on its inner wall with two pairs of vertical projections **3*a*, 3*b* extending from the partition wall 35 towards the open end 38 to form two guide grooves 31 which are symmetrical with respect to the axis of the guide capsule 3. Each guide groove 31 is provided with a step 311** at an upper portion thereof to hold the needle in place.

Above the step 311, there is provided a projection 313 for holding the needle 2 in place and for prevention of upward movement of the needle which may occur before use when the solvent container is turned upside down. Below the step 311, there is provided a projection 314 for prevention of upward movement of the needle 2 which may occur by the elasticity of the rubber stopper 14 after piercing the needle 2 into the rubber stopper 14 of the container body 1 to allow the container body 1 to communicate with a drug container or vial.

The partition wall 35 of the guide capsule 3 is provided with a through hole 34 which is coaxial with the capsule 3, through which the double-pointed needle 2 is pierced into the rubber stopper 14. In the periphery of partition wall 35, an annular groove 37 is provided for attachment of a sealing member 36 such as O-ring. The sealing member 36 is fitted in the groove 37 and pressed against the covering member 15 to provide a hermetical seal between the guide capsule 3 and the container body 1.

The connecting portion 32 of the guide capsule 3 is provided with a female screw 321 adapted to be engaged with the male screw 151 provided on the mouth 11 of the container body 1. At a lower part of the connecting portion 32 there are provided two recess or stepped portions 33 in which the fastening lobes 153 of the container body 1 are fitted and removably fixed to the guide capsule 3 by a lock ring 4 so as to avoid their disengagement from the stepped portions 33. Thus, the guide capsule 3 can not be removed from the container body 1 unless the fastening lobes 153 of the container body 1 are taken away from the stepped portions 33 of the guide capsule 3.

The double-pointed needle 2 serving as a fluid communication is arranged in the guide capsule 3, as shown in FIG. 1. The needle 2 comprises a cannula 20 and a hub 21 attached to a middle part of the cannula 20. The cannula 20 is a slender, pointed hollow member, usually of stainless steel or synthetic resin, having sharp edges at both end. The needle 2 includes two parts, an upper piercing needle 22 and a lower piercing needle 23, separated by the hub 21.

The upper piercing needle 22 may be so designed as to have an edge sharper than that of the lower piercing needle 23 to ensure that the upper piercing needle 22 is pierced into a rubber stopper 80 of the drug vial V prior to the lower piercing needle 23 being pierced into the rubber stopper 14 of the container body 1. In the above embodiment, the upper and lower piercing needles 22 and 23 are formed so as to have sharpened at the center, but they may take any configurations as occasion demands.

Further, the double-pointed needle 2 is provided with two parallel passages 25 extending therethrough to allow the solvent to flow without deformation of the container body 1. However, it is possible to use a double-pointed needle with one passage. In this case, it is necessary to deform the container body 1 by applying compressive stresses to the container body 1 to allow the solvent to flow into the drug vial.

As a material for the cannula 20, it is preferred to use stainless steel, preferably SUS 304 defined by JIS (corresponding to AISI 304) when taking a serious view of the sharpness of the needle. However, when taking a serious view of problems in waste treatment and monolithic molding properties of the needle, it is preferred to use plastics such as ABS resins, polycarbonates, high density polyethylene, and the like.

Figure 6:
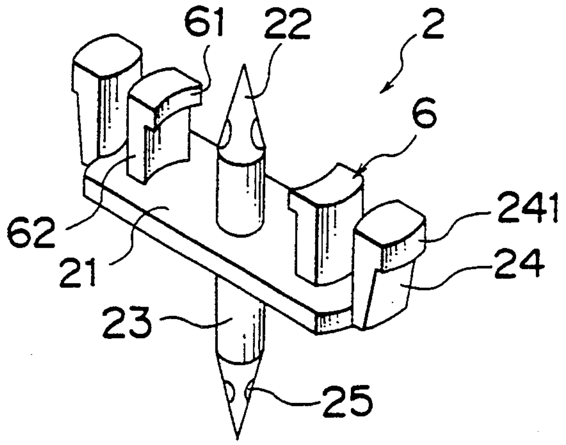
FIG. 6 is a perspective view of a double-pointed hollow needle used in the solvent container of FIG. 1.

As best shown in FIG. 6, the hub 21 of the double-pointed needle 2 is an I-shaped body, usually of a resilient plastics, having two arms 24 each extending upwardly from the end thereof and having a small, outwardly protruded portion 241 at its free end. The arms 24 are slidably arranged in the guide grooves 31 of the guide capsule 3 and the protruded portions 241 are rested on the stepped portions 311 of the needle guide grooves 31 of the guide capsule 3 so that they are disengaged from the stepped portions 311 only when a load applied to the needle 2 exceeds a predetermined value which may be determined by the size and material of the hub 21.

The hub 21 of the double-pointed needle 2 includes a pair of integrally molded hooks 6 which are arranged between the arms 24 and serve as a means for prevention of kickback caused by the elasticity of a rubber stopper 80 of the drug vial. The hook 6 has a leg 62 extending upwardly from the surface of the hub 21 for a sufficient distance and having at its free end an inwardly extending swelling 61 adapted to engage and grip the neck portion of the drug vessel.

The lock ring 4 has been provided to avoid accidental disengagement of the guide capsule 3 from the flexible container body 1.

Figure 7:
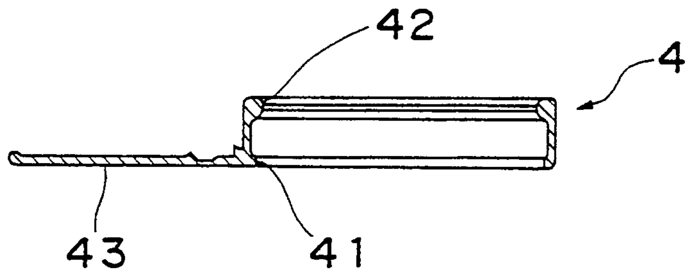
FIG. 7 is a sectional view of a lock ring used in the solvent container of FIG. 1.
Figure 8:
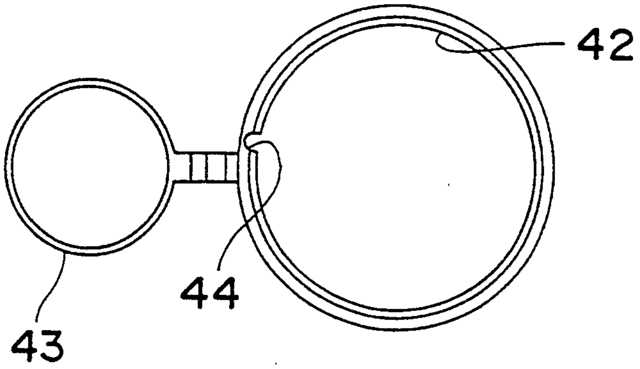
FIG. 8 is a top view of a lock ring used in the solvent container of FIG. 1.

As shown in FIGS. 7 and 8, the lock ring 4 has first and second annular projections 41 and 42 and s pulling tab 43 integrally molded therewith. The first annular projection 41 is adapted to be engaged with the covering member 15 fitted on the mouth 11 of the flexible container body 1, while the second projection 42 is adapted to be engaged with the upper end of the fastening lobes 153 engaged with the stepped portion 33 of the guide capsule 3. Further, the lock ring 4 is provided with a weakened part 44 to make it breakable.

The solvent container of the above embodiment may be assembled by screw-mounting the guide capsule 1 on the flexible container body 1, mounting the lock ring 4 on the guide capsule 3, placing the double-pointed needle 2 in the guide capsule 3, and sealing the open end of the guide capsule 3 with the sealing member 5.

Figure 19:
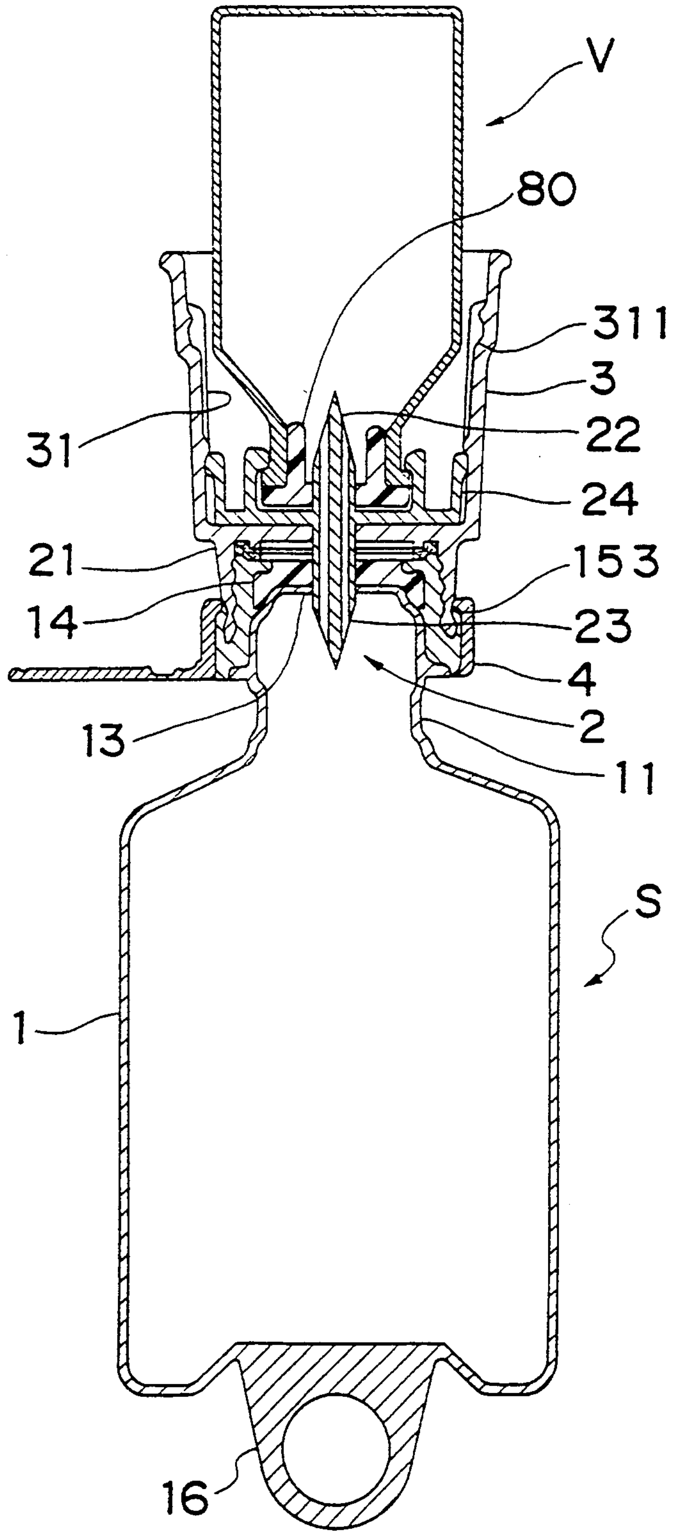
FIG. 19 is a sectional view of the solvent container of FIG. 1 with a drug vial being combined therewith.

In use, the sealing member 5 is peeled off from the open end of the guide capsule 3 and a commercially available drug vial V is pushed in the guide capsule 3 through the open end thereof until the hub 21 of the needle 2 comes into contact with the partition wall 35 of the guide capsule 3, as shown in FIG. 19.

During pushing the drug vial V in the guide capsule 3, the rubber stopper 80 of the drug vial V comes into contact with the double-pointed needle 2 and is pierced by the upper piercing needle 22 of the needle 2. Then, the mouth of the drug vial V is reached to the hub 21 of the needle 2 and the arms 24 of the hub 21 are disengaged from the steps 311 of the guide capsule 3 because of an increasing load applied to the hub 21 by the drug vial V.

Thus, the needle 2 is forced to move toward the partition wall 35 of the guide capsule 3 along the vertical guide grooves 31 thereof until the hub 21 of the needle 2 comes into contact with the partition wall 35 of the guide capsule 3. During this process, the double-pointed needle 2 pierce the rubber stopper 14 and sealing membrane 13 of the container body 1 at its lower piercing needle 23, thereby communicating the container body 1 with the drug vial V through the double-pointed needle 2. On the other hand, the hooks 6 of the hub 21 are spread out by the mouth of the drug vial V and then returned to the original positions. At the same time, the swellings 61 of the hooks 6 engage with and grip the neck portion of the drug vial V, thus making it possible to prevent the drug vial V from kickback which may be caused by the elasticity of the rubber stopper 80 just when the double-pointed needle 2 is pierced into the rubber stopper 80 of the drug vial V.

The drug in the drug vial V may be mixed with the solvent in the container body 1 in the following manner.

Firstly, the solvent container coupled to the drug vial V is turned upside down, thereby allowing the solvent to flow into the drug vial V where the solvent is mixed with the dry drug. If necessary, the container body 1 may be pressed and deformed by hand to accelerate flow of the solvent. Then, the solvent container is turned upside down again so that the resultant drug solution in the drug vial V is returned to the container body 1. If the container body 1 has been deformed, the flow of the drug solution is accelerated by a pumping action of the container body 1 since the deformed container 1 is restored to the original state by its elasticity.

The guide capsule 3 is removed from the flexible container body 1 by tearing the lock ring 4 at its weakened part 44 to remove the lock ring 4, disengaging the fastening lobes 153 from the stepped portions 33 of the guide capsule 3, and then turning the guide capsule 3 in the direction of loosening the screw. Then, the container body 1 is hanged at its tab 16 on a hanger (not shown) and connected to an infusion set by piercing a hollow spike of the infusion set into the rubber stopper 14 on the mouth 11 of the container body 1, thus making it possible to administer the resultant solution to a patient. Thus, the mouth 11 of the container body 1 is also used as an outlet for a drug solution prepared by mixing the solvent with the drug in the vial V.

In the above embodiment, the guide capsule 3 is provided with two guide grooves 31, but it may have one guide groove, or more than three guide grooves. Also, the guide grooves 31 are constituted by a pair of vertical projections 3_a_ or 3_b_ integrally molded with the guide capsule 3, they may be formed directly in the barrel of the guide capsule 3.

Figure 9:
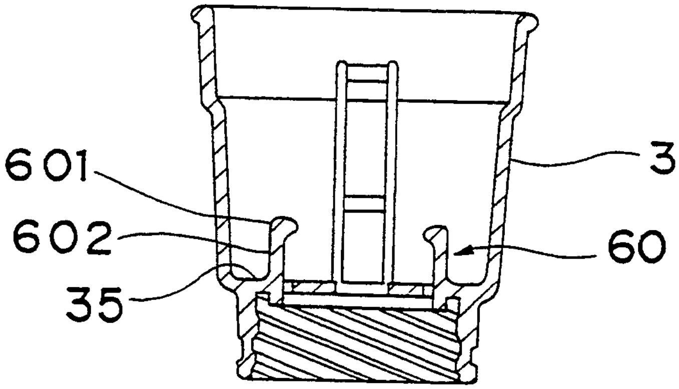
FIG. 9 is a sectional view of a guide capsule used in another embodiment of the present invention.
Figure 10:
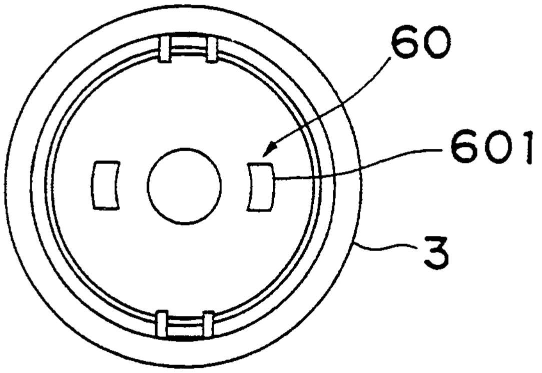
FIG. 10 is a bottom view of the guide capsule of FIG. 9.

Further, the means for prevention of kickback of the drug vial may be provided on the guide capsule 3 as shown in FIGS. 9 and 10. In this embodiment, the means for prevention of kickback is constituted by a pair of hooks 60 each having a swelling 601 and a leg 602. The hooks 60 are integrally molded with the partition wall 35 of the guide capsule 3 in such a manner that they are symmetrical with respect to the axis of the guide capsule 3 and that the plane passing through their center lines perpendicular to the partition wall 35 intersects at a right angle with the plane containing the vertical center lines of the diametrically arranged guide grooves 31 of the guide capsule 3. Thus, the plane passing through the center lines of hooks 60 intersects at a right angle with the surface of the body of the I-shaped hub 201 of the needle 20.

Figure 11:
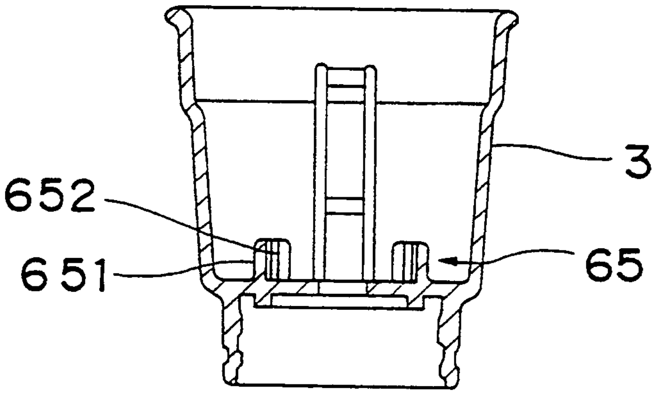
FIG. 11 is a sectional view of a guide capsule used in still another embodiment of the present invention.
Figure 12:
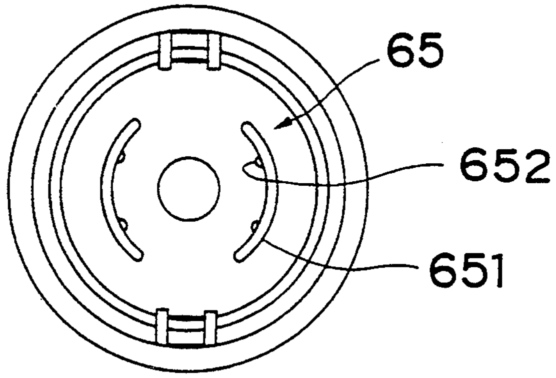
FIG. 12 is a bottom view of the guide capsule of FIG. 11.

FIGS. 11 and 12 show another modified form of a guide capsule 3. In this embodiment, the guide capsule 3 has a structure similar to that of the guide capsule of FIG. 11 except that a means for prevention of kickback of the drug vial includes a pair of projections 651 with a plurality of ribs 652 adapted to be engaged with the mouth of the drug vial to hold it in position. The projections 651 are molded integrally with the partition wall of the guide capsule 3 so that they have an arched cross section and are symmetrical with respect to the axis of the guide capsule 3.

If the means for prevention of kickback of the drug vial is provided on the hub of the double-pointed needle and if the guide capsule is not provided with the means for prevention of kickback of the drug vial, the hub of the double-pointed needle may be formed into a crossed body with four arms 24 each extending upwardly from the end thereof and having a small, outwardly protruded portion 241 at its free end.

Figure 13:
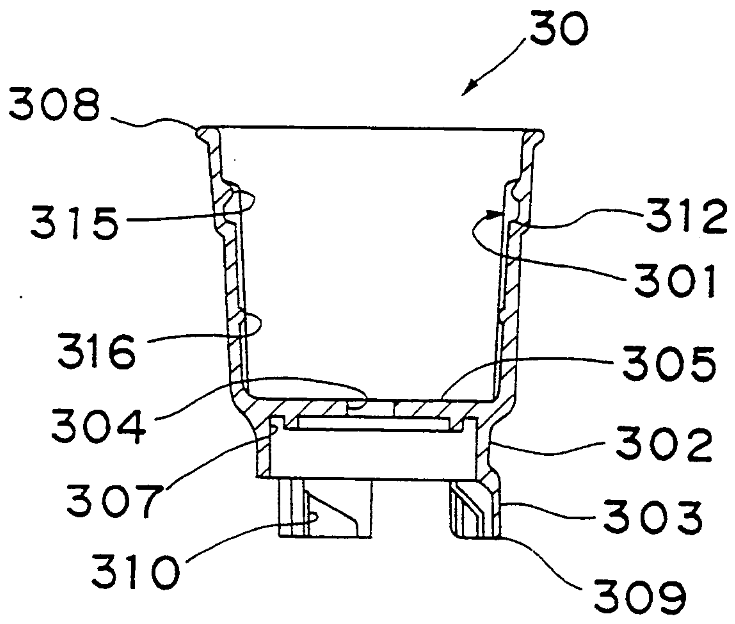
FIG. 13 is a sectional view of a guide capsule used in still another embodiment of the present invention.
Figure 14:
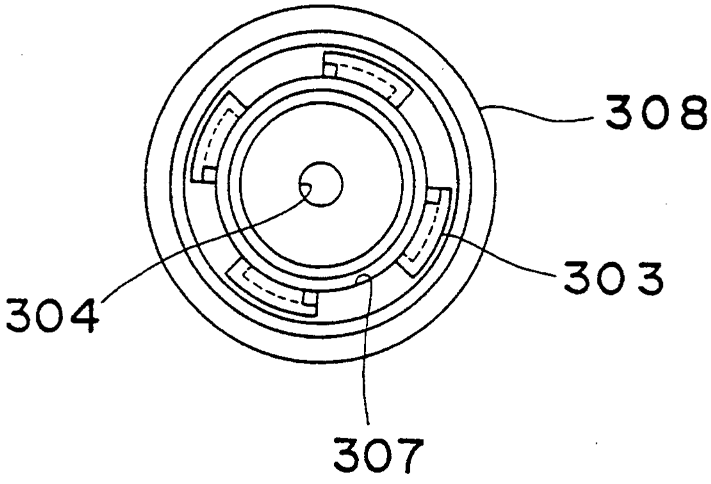
FIG. 14 is a bottom view of the guide capsule of FIG. 13.

The connecting portion 32 of the guide capsule 3 may be modified so as to have a configuration as illustrated in FIGS. 13 and 14. In this embodiment, a guide capsule 30 has a connecting portion 302 with four coupling legs 303 integrally molded with the connecting portion 302. The coupling legs 303 have a configuration complementing coupling projections 102 provided on the mouth 101 of a solvent container 10 shown in FIG. 17. Each coupling leg 303 has a groove 310 for preventing the guide capsule 30 from rotation in the direction which loosens the coupling between the guide capsule 30 and solvent container 10.

Other parts of the guide capsule 30 are the same as those of the guide capsule 3. Thus, vertical guide grooves 301, a partition wall 305 with a through hole 304, an annular groove 307 for insertion of a sealing member such as O-ring (not shown), an open end 308, a connecting end 309, steps 312 and projections 315 and 316 respectively correspond to the guide grooves 31, partition wall 35 with through hole 34, annular groove 37, open end 38, connecting end 309, steps 311 and projections 313 and 314 of the guide capsule 3 of FIG. 3.

Figure 15:
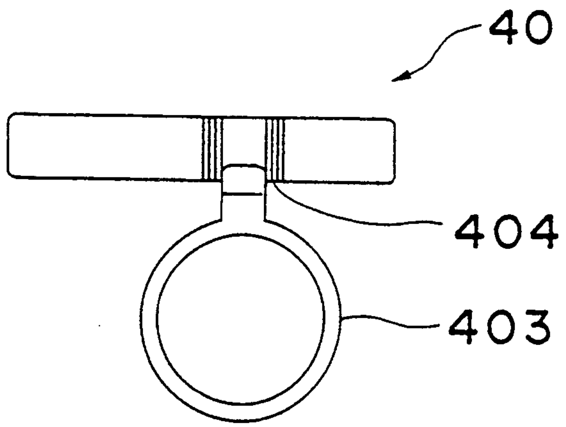
FIG. 15 is a sectional view of a lock ring used in another embodiment of the present invention.
Figure 16:
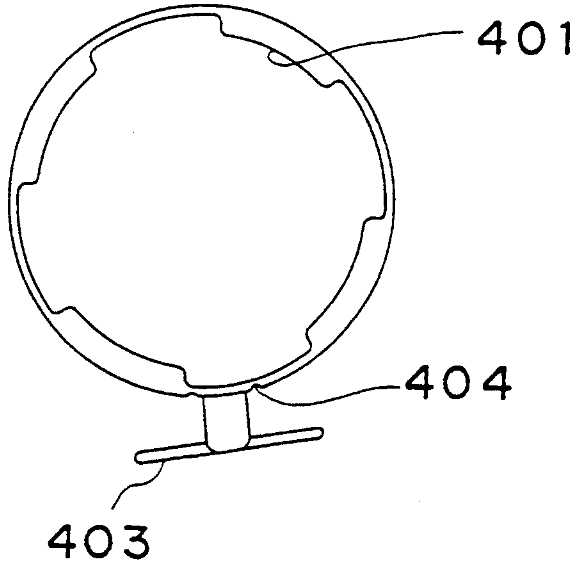
FIG. 16 is a top view of a lock ring used in the solvent container of FIG. 15.
Figure 17:
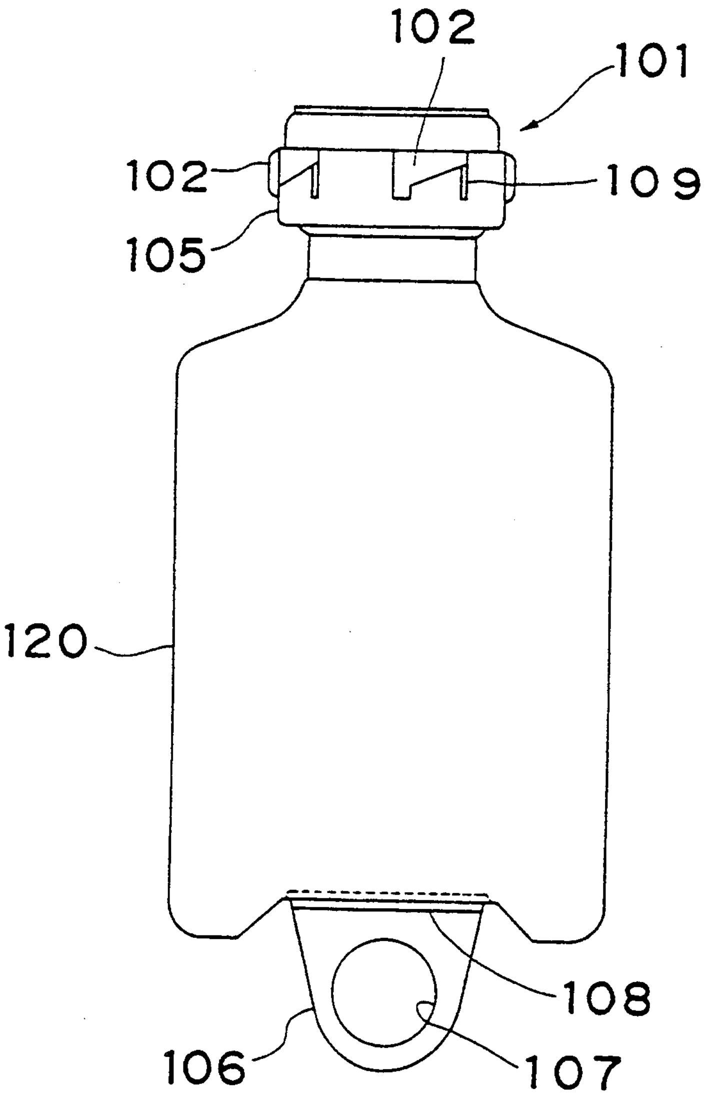
FIG. 17 is a side view of a flexible container body used in another embodiment of the present invention.
Figure 18:
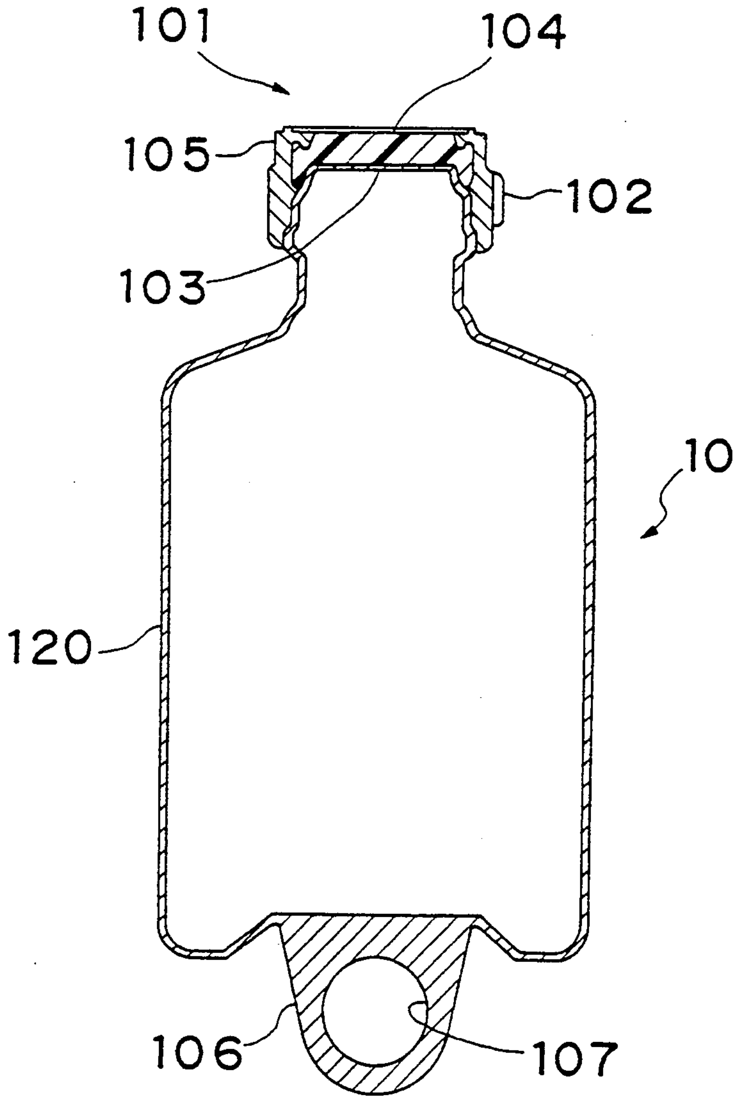
FIG. 18 is a sectional view of the container body of FIG. 17.

The guide capsule 30 of FIGS. 13 and 14 is used in combination with a lock ring 40 shown in FIGS. 15 and 16 and a flexible container body 10 shown in FIGS. 17 and 18.

In the embodiment of FIGS. 17 and 18, the solvent container includes a flexible container body 10 provided at a periphery of its mouth 101 with four coupling projections 102 each having a configuration complementary with a coupling leg 303 of the guide capsule 30 shown in FIG. 13. The mouth 101 is closed by an integrally molded sealing membrane 103 and a rubber stopper 104 pressed against the mouth 101 by a covering member 105. At the bottom, there is a tab 106 having a hole 107 and being connected to the bottom by a integrally hinged portion 108. Also, the covering member 105 is provided with ribs 109 adapted to be engaged with the grooves 310 of the guide capsule 30 to prevent it from rotary motion.

As shown in FIGS. 15 and 16, the lock ring 40 is provided with projections 401, a pulling ring 403 and weakened part 404. The projections 401 are adapted to be fitted in recesses, which are formed between the guide capsule 30 and the solvent container 10 when the coupling legs 303 of the guide capsule 30 are coupled to the coupling projections 102 of the container body 10, to prevent the guide capsule 30 and the container body 10 from relative rotary motion.

As will be understood from the above, it is possible with the present invention to produce a solvent container which is easy to operate and makes it possible to aseptically mix the drug with the solvent. Further, it is possible to provide a solvent container at a moderate price as it is constituted by small number of parts. In addition, there is no fear of leakage of the drug solution from the container body as the mouth of the container body is covered with a self-sealing means. According to the present invention, it is also possible to provide a compact solvent container as the cannula of the double-pointed needle can be minimized by provision of a means for prevention of kickback caused by the elasticity of a rubber stopper.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A solvent container with a means for communicating with a drug vial, comprising:

a flexible container body containing a solvent and having a mouth covered with a self-sealing means;

a guide capsule having an open end at one end and being removably mounted on the mouth of said flexible container body at the other end, said open end being sealed by a sealing member prior to insertion of a drug vial;

a double-pointed needle having a sharp piercing edge at each end and a hub at its central part, said needle being slidably arranged in said guide capsule to constitute a means for communicating with a drug vial in cooperation with said guide capsule;

an inner wall of said guide capsule having one or more vertical guide grooves for holding said double-pointed needle and for guiding said double-pointed needle towards the mouth of said flexible container, said guide capsule having a partition wall with a hole for insertion of the piercing edge of said double-pointed needle into said mouth of said container body through said self-sealing means; and wherein said guide grooves extend above and below said hub and extend to said partition wall.

2. The solvent container claimed in claim 1 wherein said hub has arms provided at free ends thereof and adapted to be held in the guide grooves of the guide capsule.

3. The solvent container claimed in claim 2 wherein each guide groove of said guide capsule is provided with a stepped portion on which the arms of the hub are rested to hold said needle in place until a load applied to the needle exceeds a predetermined value.

4. The solvent container claimed in claim 2 wherein the hub of the hollow needle is provided with a means for prevention of kickbacks of a drug vial caused by the elasticity of said self-sealing means.

5. The solvent container claimed in claim 2 wherein the partition wall of said guide capsule has a means for preventing said double-pointed needle from kickbacks caused by the elasticity of said self-sealing means.

6. The solvent container claimed in claim 2 wherein the guide capsule is provided in its guide groove with a projection for preventing an upward movement of the double-pointed needle, which may occur after piercing the double-pointed needle into the self sealing means of the container body.

* * * * *